United States Patent
Gerber et al.

(10) Patent No.: US 9,968,721 B2
(45) Date of Patent: *May 15, 2018

(54) MONITORING FLUID VOLUME FOR PATIENTS WITH RENAL DISEASE

(71) Applicant: Medtronic, Inc., Minneapolis, MN (US)

(72) Inventors: Martin Gerber, Maple Grove, MN (US); John Burnes, Coon Rapids, MN (US); Suping Lyu, Maple Grove, MN (US); VenKatesh R. Manda, Stillwater, MN (US); Bryant Pudil, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 77 days.

This patent is subject to a terminal disclaimer.

(21) Appl. No.: 14/554,338

(22) Filed: Nov. 26, 2014

(65) Prior Publication Data

US 2015/0080682 A1 Mar. 19, 2015

Related U.S. Application Data

(62) Division of application No. 13/424,467, filed on Mar. 20, 2012, now Pat. No. 8,926,542.
(Continued)

(51) Int. Cl.
*A61M 37/00* (2006.01)
*A61M 1/16* (2006.01)
(Continued)

(52) U.S. Cl.
CPC ......... *A61M 1/1603* (2014.02); *A61B 5/0031* (2013.01); *A61B 5/026* (2013.01);
(Continued)

(58) Field of Classification Search
CPC ...... A61M 2205/33; A61M 2205/3303; A61M 1/1603; A61M 1/1613; A61M 1/3607;
(Continued)

(56) References Cited

U.S. PATENT DOCUMENTS

| | | | |
|---|---|---|---|
| 3,608,729 | A | 9/1971 | Haselden |
| 3,669,878 | A | 6/1972 | Marantz |

(Continued)

FOREIGN PATENT DOCUMENTS

| | | |
|---|---|---|
| CN | 0101193667 | 6/2008 |
| CN | 103037917 | 4/2013 |

(Continued)

OTHER PUBLICATIONS

Wang, Fundamentals of intrathoracic impedance monitoring in heart failure, Am. J. Cardiology, 2007, 3G-310: Suppl.
(Continued)

*Primary Examiner* — Leslie Deak
(74) *Attorney, Agent, or Firm* — Kenneth Collier; Roger Hahn

(57) ABSTRACT

A method includes monitoring an indicator of fluid volume of a patient via a sensor device, and setting an initial fluid volume removal prescription for a blood fluid removal session based on the monitored indicator of fluid volume. The method may further include transmitting data regarding the indicator of fluid volume from the implantable sensor device to fluid removal device. The system includes a blood fluid removal device and control electronics configured to set the initial fluid removal volume and rate prescription. In some embodiments, the fluid removal device sets or calculates the initial fluid volume removal prescription based on the data received from the implantable sensor. The indicator of fluid volume may be an indicator of tissue fluid volume or an indicator of blood fluid volume.

17 Claims, 10 Drawing Sheets

Related U.S. Application Data

(60) Provisional application No. 61/480,539, filed on Apr. 29, 2011, provisional application No. 61/480,544, filed on Apr. 29, 2011, provisional application No. 61/480,541, filed on Apr. 29, 2011, provisional application No. 61/480,535, filed on Apr. 29, 2011, provisional application No. 61/480,532, filed on Apr. 29, 2011, provisional application No. 61/480,530, filed on Apr. 29, 2011, provisional application No. 61/480,528, filed on Apr. 29, 2011.

(51) Int. Cl.

| | | |
|---|---|---|
| A61B 5/145 | (2006.01) | |
| A61B 5/00 | (2006.01) | |
| A61B 5/026 | (2006.01) | |
| A61B 5/053 | (2006.01) | |
| A61M 1/34 | (2006.01) | |
| B01D 65/02 | (2006.01) | |
| A61M 1/00 | (2006.01) | |
| A61B 5/0295 | (2006.01) | |
| A61M 1/14 | (2006.01) | |
| B01D 61/00 | (2006.01) | |
| B01D 61/32 | (2006.01) | |
| A61M 1/36 | (2006.01) | |
| A61M 1/28 | (2006.01) | |

(52) U.S. Cl.
CPC ............ *A61B 5/0295* (2013.01); *A61B 5/053* (2013.01); *A61B 5/0537* (2013.01); *A61B 5/145* (2013.01); *A61B 5/14503* (2013.01); *A61B 5/14535* (2013.01); *A61B 5/14539* (2013.01); *A61B 5/14546* (2013.01); *A61B 5/4836* (2013.01); *A61B 5/4848* (2013.01); *A61B 5/4875* (2013.01); *A61B 5/6866* (2013.01); *A61B 5/7282* (2013.01); *A61M 1/00* (2013.01); *A61M 1/14* (2013.01); *A61M 1/16* (2013.01); *A61M 1/1601* (2014.02); *A61M 1/1605* (2014.02); *A61M 1/1607* (2014.02); *A61M 1/1613* (2014.02); *A61M 1/28* (2013.01); *A61M 1/34* (2013.01); *A61M 1/342* (2013.01); *A61M 1/3607* (2014.02); *A61M 1/3609* (2014.02); *A61M 1/3672* (2013.01); *B01D 61/00* (2013.01); *B01D 61/32* (2013.01); *B01D 65/02* (2013.01); *A61B 2560/0223* (2013.01); *A61M 2202/0498* (2013.01); *A61M 2205/04* (2013.01); *A61M 2205/18* (2013.01); *A61M 2205/33* (2013.01); *A61M 2205/3303* (2013.01); *A61M 2205/3334* (2013.01); *A61M 2205/3523* (2013.01); *A61M 2205/50* (2013.01); *A61M 2205/52* (2013.01); *A61M 2205/60* (2013.01); *A61M 2205/70* (2013.01); *A61M 2230/00* (2013.01); *A61M 2230/005* (2013.01); *A61M 2230/20* (2013.01); *A61M 2230/207* (2013.01); *A61M 2230/208* (2013.01); *A61M 2230/65* (2013.01); *B01D 2321/12* (2013.01); *B01D 2321/40* (2013.01)

(58) Field of Classification Search
CPC ........ A61M 1/3605; A61M 1/14; A61M 1/34; A61B 5/4836; A61B 5/4848; A61B 5/48753
USPC .... 604/5.01, 5.04, 6.09, 6.11; 210/645, 646, 210/746
See application file for complete search history.

(56) References Cited

U.S. PATENT DOCUMENTS

| | | |
|---|---|---|
| 3,669,880 A | 6/1972 | Marantz |
| 3,850,835 A | 11/1974 | Marantz |
| 3,884,808 A | 5/1975 | Scott |
| 3,989,622 A | 11/1976 | Marantz |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,678,408 A | 7/1987 | Mason |
| 4,685,903 A | 8/1987 | Cable |
| 4,750,494 A | 6/1988 | King |
| 4,826,663 A | 5/1989 | Alberti |
| 4,828,693 A | 5/1989 | Lindsay |
| 5,080,653 A | 1/1992 | Voss |
| 5,092,886 A | 3/1992 | Dobos-Hardy |
| 5,097,122 A | 3/1992 | Coiman |
| 5,127,404 A | 7/1992 | Wyborny |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,468,388 A | 11/1995 | Goddard |
| 5,507,723 A | 4/1996 | Keshaviah |
| 5,651,893 A | 7/1997 | Kenley |
| 5,683,432 A | 11/1997 | Goedeke |
| 5,744,031 A | 4/1998 | Bene |
| 5,762,782 A | 6/1998 | Kenley |
| 5,902,336 A | 5/1999 | Mishkin |
| 5,944,684 A | 8/1999 | Roberts |
| 6,048,732 A | 4/2000 | Anslyn |
| 6,052,622 A | 4/2000 | Holmstrom |
| 6,058,331 A | 5/2000 | King |
| 6,156,002 A | 12/2000 | Polaschegg et al. |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,505,075 B1 | 1/2003 | Weiner |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,627,164 B1 | 9/2003 | Wong |
| 6,676,608 B1 | 1/2004 | Keren |
| 6,689,083 B1 | 2/2004 | Gelfand |
| 6,706,007 B2 | 3/2004 | Gelfand |
| 6,711,439 B1 | 3/2004 | Bradley |
| 6,726,647 B1 | 4/2004 | Sternby |
| 6,780,322 B1 | 8/2004 | Bissler |
| 6,818,196 B2 | 11/2004 | Wong |
| 6,878,283 B2 | 4/2005 | Thompson |
| 6,887,214 B1 | 5/2005 | Levin |
| 6,890,315 B1 | 5/2005 | Levin |
| 6,960,179 B2 | 11/2005 | Gura |
| 7,074,332 B2 | 7/2006 | Summerton |
| 7,077,819 B1 | 7/2006 | Goldau |
| 7,131,956 B1 | 11/2006 | Pirazzoli |
| 7,175,809 B2 | 2/2007 | Gelfand |
| 7,208,092 B2 | 4/2007 | Micheli |
| 7,276,042 B2 | 10/2007 | Polaschegg |
| 7,399,289 B2 | 7/2008 | Gelfand |
| 7,500,958 B2 | 3/2009 | Asbrink |
| 7,566,432 B2 | 7/2009 | Wong |
| 7,575,564 B2 | 8/2009 | Childers |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |

(56) References Cited

U.S. PATENT DOCUMENTS

| | | |
|---|---|---|
| 7,754,852 B2 | 7/2010 | Burnett |
| 7,756,572 B1 | 7/2010 | Fard |
| 7,775,983 B2 | 8/2010 | Zhang |
| 7,776,210 B2 | 8/2010 | Rosenbaum |
| 7,785,463 B2 | 8/2010 | Bissler |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,291 B2 | 6/2011 | Sternby |
| 7,967,022 B2 | 6/2011 | Grant |
| 7,981,082 B2 | 7/2011 | Wang |
| 8,000,000 B2 | 8/2011 | Greenberg |
| 8,034,161 B2 | 10/2011 | Gura |
| 8,070,709 B2 | 12/2011 | Childers |
| 8,096,969 B2 | 1/2012 | Roberts |
| 8,105,260 B2 | 1/2012 | Tonelli |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding |
| 8,409,441 B2 | 4/2013 | Wilt |
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,926,542 B2 * | 1/2015 | Gerber ............... A61B 5/0537 210/645 |
| 2002/0042561 A1 | 4/2002 | Schulman |
| 2002/0112609 A1 | 8/2002 | Wong |
| 2003/0080059 A1 | 5/2003 | Peterson |
| 2003/0097086 A1 | 5/2003 | Gura |
| 2003/0105435 A1 | 6/2003 | Taylor |
| 2003/0114787 A1 | 6/2003 | Gura |
| 2004/0019312 A1 | 1/2004 | Childers |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0126998 A1 | 6/2005 | Childers |
| 2005/0131331 A1 | 6/2005 | Kelly |
| 2005/0150832 A1 | 7/2005 | Tsukamoto |
| 2005/0234381 A1 | 10/2005 | Niemetz |
| 2005/0236330 A1 | 10/2005 | Nier |
| 2005/0274658 A1 | 12/2005 | Rosenbaum |
| 2006/0025661 A1 | 2/2006 | Sweeney |
| 2006/0058731 A1 | 3/2006 | Burnett |
| 2006/0195064 A1 | 8/2006 | Plahey |
| 2006/0217771 A1 | 9/2006 | Soykan |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0213653 A1 | 9/2007 | Childers |
| 2007/0215545 A1 | 9/2007 | Bissler |
| 2007/0255250 A1 | 11/2007 | Moberg |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0215247 A1 | 9/2008 | Tonelli |
| 2008/0253427 A1 | 10/2008 | Kamen |
| 2009/0020471 A1 | 1/2009 | Tsukamoto |
| 2009/0101577 A1 | 4/2009 | Fulkerson |
| 2009/0124963 A1 | 5/2009 | Hogard |
| 2009/0127193 A1 | 5/2009 | Updyke |
| 2009/0171261 A1 | 7/2009 | Sternby |
| 2009/0264776 A1 * | 10/2009 | Vardy ............... A61B 5/0537 600/506 |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0010429 A1 | 1/2010 | Childers |
| 2010/0042035 A1 | 2/2010 | Moissl |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0259276 A1 | 10/2012 | Childers |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |

(56) References Cited

U.S. PATENT DOCUMENTS

| | | |
|---|---|---|
| 2012/0277655 A1 | 11/2012 | Gerber |
| 2012/0277722 A1 | 11/2012 | Gerber |
| 2013/0037465 A1 | 2/2013 | Heyes |
| 2013/0062265 A1 | 3/2013 | Balschat |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky) Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0250427 A1 | 9/2015 | Soykan |
| 2015/0352269 A1 | 12/2015 | Gerber |
| 2015/0367054 A1 | 12/2015 | Gerber |
| 2016/0206801 A1 | 7/2016 | Gerber |
| 2016/0331884 A1 | 11/2016 | Sigg |

FOREIGN PATENT DOCUMENTS

| | | |
|---|---|---|
| EP | 266795 A2 | 11/1987 |
| EP | 0272414 | 10/1991 |
| EP | 0330892 | 7/1994 |
| EP | 1124599 | 5/2000 |
| EP | 1175238 | 11/2000 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 2701596 | 3/2014 |
| EP | 1582226 | 1/2016 |
| JP | 2002542900 | 12/2002 |
| JP | 2003235965 | 8/2003 |
| JP | 5099464 | 10/2012 |
| WO | 9503839 | 2/1995 |
| WO | 9937342 | 7/1999 |
| WO | 0057935 | 10/2000 |
| WO | 0066197 | 11/2000 |
| WO | 0170307 A1 | 9/2001 |
| WO | 0185295 A2 | 9/2001 |
| WO | 0066197 A1 | 11/2001 |
| WO | 0185295 | 11/2001 |
| WO | 0185295 A2 | 11/2001 |
| WO | 2002013691 | 2/2002 |
| WO | 03043677 A2 | 5/2003 |
| WO | 03043680 | 5/2003 |
| WO | 03051422 A2 | 6/2003 |
| WO | 2004008826 | 1/2004 |
| WO | 2004009156 | 1/2004 |
| WO | 2004009158 | 1/2004 |
| WO | 2004030716 A2 | 4/2004 |
| WO | 2004030717 A2 | 4/2004 |
| WO | 2004064616 A2 | 8/2004 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | 2008037410 | 4/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009094184 | 7/2009 |
| WO | 2009157877 A1 | 12/2009 |
| WO | 2009157878 A1 | 12/2009 |
| WO | 2010028860 A1 | 2/2010 |
| WO | 2010024963 | 3/2010 |
| WO | 2010028860 | 3/2010 |
| WO | 2010033314 | 3/2010 |
| WO | 2010033699 | 3/2010 |
| WO | 2010077851 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | 2011137693 | 11/2011 |
| WO | 2012042323 | 4/2012 |
| WO | 2012050781 | 4/2012 |
| WO | 2012051996 | 4/2012 |
| WO | 2012148781 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013101292 A3 | 10/2013 |
| WO | 2014066254 | 5/2014 |
| WO | 2014066255 | 5/2014 |
| WO | 2014077082 | 5/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

Bleyer, et. al., Sudden and cardiac death rates in hemodialysis patients, Kidney International, 1999, 1553-1559 : 55.

(56) References Cited

OTHER PUBLICATIONS

Brynda, et. al., The detection of toman 2-microglcbuiin by grating coupler immunosensor with three dimensional antibody networks. Biosensors & Bioelectronics, 1999, 363-368, 14(4).
Hemametrics, Crit-Line Hematocrit Accuracy, 2003, 1-5, vol. 1, Tech Note No. 11 (Rev. D).
Nedelkov, et. al., Design of buffer exchange surfaces and sensor chips for biosensor chip mass spectrometry, Proteomics, 2002, 441-446, 2(4).
PCT/US/2012/034327, International Search Report, Aug. 13, 2013.
PCT/US/2012/034329, International Search Report, Dec. 3, 2012.
PCT/US2012/034331, International Search Report, Jul. 9, 2012.
PCT/US2012/034334, International Search Report, Jul. 6, 2012.
PCT/US2012/034335, International Search Report, Sep. 5, 2012.
Roberts M, The regenerative dialysis (REDY) sorbent system. Nephrology, 1998, 275-278:4.
Siegenthalar, et. al., Pulmonary fluid status monitoring with intrathoracic impedance, Journal of Cli.
Zhong, et. al., Miniature urea sensor based on H(+)-ion sensitive field effect transistor and its application in clinical analysis, Chin. J. Biotechnol., 1992, 57-65. 8(1).
Overgaard, et. al., Activity-induced recovery of excitability in K+-depressed rat soieus muscle, Am. J. P.
Overgaard. et. al., Relations between excitability and contractility in rate soleus'muscle: role of the Na+—K+ pump and Na+—K—S gradients. Journal of Physiology, 1999, 215-225, 518(1).
PCT/US2012/034330, International Search Report, Aug. 28, 2012.
PCT/US2012/034332, International Search Report, Jul. 5, 2012.
Secemsky, et. al, High prevalence of cardiac autonomic dysfunction and T-wave alternans in dialysis patients. Heart Rhythm, Apr. 2011, 592-598 : vol. 8, No. 4.
Wang, Fundamentals of intrathoracic impedance monitoring in heart failure, Am. J. Cardiology, 2007, 3G-10G : Suppl.
Wei, et. al., Fullerene-cryptand coated piezoelectric crystal urea sensor based on urease, Analytica Chimica Acta, 2001,77-85:437.
Redfield, et. al, Restoration of renal response to atria! natriuretic factor in experimental low-output heat failure, Am. J. Physiol., 1989, R917-923:257.
Rogoza, et. al., Validation of A&D UA-767 device for the self-measurement of blood pressure, Blood Pressure Monitoring, 2000, 227-231, 5(4).
Ronco, et. al., Cardiorenal Syndrome, J. Am. Coll. Cardiol., 2008, 1527-1539:52.
PCT/US2012/034329, International Preliminary Report on Patentability, Oct. 29, 2013.
MacLean, et, al., Effects of hindlimb contraction on pressor and muscle interstitial metabolite responses in the cat, J. App. Physiol., 1998, 1583-1592, 85 (4).
Lima, et. al., An electrochemical sensor based on nanostructure hollsndite-type manganese oxide for detection of potassium ion, Sensors, 2009, 6613-8625, 9.
PCT/US2012/034335, International Preliminary Report on Patentability, Nov. 7, 2013.
Gambro AK 96 Dialysis Machine Operator's Manual, Dec. 2012.
U.S. Appl. No. 13/757,794, filed Feb. 2, 2013.
U.S. Appl. No. 13/757,722, filed Feb. 1, 2013.
U.S. Appl. No. 13/837,287, filed Mar. 15, 2013.
U.S. Appl. No. 13/757,792, filed Feb. 2, 2013.
U.S. Appl. No. 13/791,755, filed Mar. 8, 2013.
PCT/US2014/014357 International Search Report and Written Opinion.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
The FHN Trial Group. In-Center. Hemodialysis Six Times per Week versus Three Times per Week, New England Journal of Medicine, 2010 Abstract.
U.S. Appl. No. 13/757,693, filed Feb. 1, 2013.
Coast, et al. 1990, An approach to Cardiac Arrhythmia analysis Using Hidden Markov Models, IEEE Transactions on Biomedical Engineering. 1990, 37 (9):826-835.
PCT/US2012/034330, International Preliminary Report on Patentability, Oct. 29, 2013.
PCT Application, PCT/US20013/020404, filed Jan. 4, 2013.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2012/034333, International Preliminary Report on Patentability, Oct. 29, 2013.
PCT/US2012/034333, International Search Report, Aug. 29, 2013.
U.S. Appl. No. 13/757,794, filed Feb. 2, 2012.
Bleyer, et. al., Sudden and cardiac death rated in hemodialysis patients, Kidney International. 1999, 1553-1559: 55.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
U.S. Appl. No. 13/424,517 IDS, filed Aug. 2, 2012.
U.S. Appl. No. 13/424,517, IDS filed Dec. 2, 2013.
PCT/US2012/034332, Internatonal Preliminary Report on Patentability, Oct. 29, 2013.
PCT/US2012/034303, Internationa Search Report, Jul. 6, 2013.
PCT/US2012/034327, International Preliminary Report on Patentability, Oct. 29, 2013.
Zoccali, Pulmonary Congestion Predicts Cardiac Events and Mortality in ESRD, Clinical Epidemiology, J. Am Soc Nephrol 24:639-646, 2013.
Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
Whitman, CKD and Sudden Cardiac Death: Epidemiology, Mechanisms, and Therapeutic Approaches, J Am Soc Nephrol, 23:1929-1939, 2012.
Hall, Hospitalization for Congestive Heart Failure: United States, 2000-2010, NCHS Data Brief, No. 108, Oct. 2012.
Albert, Fluid Management Strategies in Heart Failure, Critical Care Nurse, 32:20-32, 2012.
PCT/US2014/065201 International Search Report mailed May 26, 2015.
John Wm Agar: "Review: Understnading sorbent dialysis systems," Nephrology, vol. 15, No. 4, Jun. 1, 2010, pp. 406-411.
Office Action in U.S. Appl. No. 14/554,272 Dated Aug. 8, 2016.
Office Action in U.S. Appl. No. 13/424,467 Dated Oct. 16, 2013.
Office Action in U.S. Appl. No. 13/424,467 Dated Mar. 3, 2014.
Office Action in U.S. Appl. No. 13/424,490 Dated Oct. 22, 2013.
Office Action in U.S. Appl. No. 13/424,490 Dated Mar. 10, 2014.
Office Action in U.S. Appl. No. 13/424,490 Dated Jul. 14, 2014.
Office Action in U.S. Appl. No. 13/424,490 Dated Dec. 5, 2014.
Office Action in U.S. Appl. No. 13/424,525 dated Sep. 29, 2014.
Office Action in U.S. Appl. No. 13/424,525 dated May 6, 2015.
Office Action in U.S. Appl. No. 13/424,525 dated Aug. 11, 2015.
Office Action in U.S. Appl. No. 13/424,525 dated Oct. 26, 2016.
Office Action in U.S. Appl. No. 13/424,454 Dated Oct. 17, 2013.
Office Action in U.S. Appl. No. 13/424,454 Dated Mar. 10, 2014.
Office action in U.S. Appl. No. 13/424,429 dated Oct. 15, 2015.
Office Action in U.S. Appl. No. 12/571,127 dated Feb. 27, 2014.
Office Action in U.S. Appl. No. 12/571,127 dated Jul. 6, 2015.
Office Action in U.S. Appl. No. 12/571,127 dated Dec. 17, 2015.
Office Action in Chinese Application No. 201280020937.4 dated Oct. 22, 2016.
Office Action in Japanese Application No. 2014-508434 dated Nov. 16, 2015.
Office Action in Japanese Application No. 2014-508434 dated Dec. 8, 2014.
Office Action in Japanese Application No. 2014-508434 dated Nov. 4, 2016.
Office Action in European Application No. 12717019.9 dated Feburary 16, 2017.
Office Action in Chinese Application No. 201510511657.9 dated May 10, 2017.

(56) References Cited

OTHER PUBLICATIONS

Office Action in European Application No. EP 12717021.5 dated Feb. 3, 2017.
Office Action in Chinese Application No. 201510593695.3 dated Jul. 12, 2017.

* cited by examiner

MONITORING FLUID VOLUME FOR PATIENTS WITH RENAL DISEASE

RELATED APPLICATION

This application claims priority to U.S. Provisional Application No. 61/480,539, U.S. Provisional Application No. 61/480,544, filed Apr. 29, 2011, U.S. Provisional Application No. 61/480,541, U.S. Provisional Application No. 61/480,535, U.S. Provisional Application No. 61/480,532, U.S. Provisional Application No. 61/480,530, U.S. Provisional Application No. 61/480,528, and U.S. application Ser. No. 13/424,467, all of which application are hereby incorporated by reference in its entirety to the extent that it does not conflict with the disclosure presented herein.

FIELD

The present disclosure relates generally to devices, systems and methods for monitoring fluid volume in patients with renal disease.

BACKGROUND

Current methods used to manage stage 3 to stage 4 chronic kidney disease patients typically involve monitoring the patient's symptoms and glomerular filtration rate (GFR). Prior to the patient reaching a point where additional therapy in the form of supplemental hemodialysis is needed, an access point (fistula) will typically be created by surgically diverting an artery to a vein. The fistula usually takes four to six weeks to mature, but can take up to six months to mature and be ready for hemodialysis. In some situations, the patient's kidneys decline to rapidly such that the fistula has not matured before they require dialysis treatment. In such situations, a central venous catheter may be used until the fistula matures. However, central venous catheters are more infection prone and suffer from clotting and fatigue issues. Accordingly, it is desired to ensure that the fistula matures prior to the patient requiring hemodialysis. Unfortunately, it can be difficult to predict when a stage 3 or stage 4 chronic kidney disease patient will need supplemental hemodialysis treatment and current methods for sufficiently monitoring such patients are lacking.

Once a patient begins undergoing dialysis treatment or another fluid removal processes, such as ultrafiltration, it can be difficult to determine how much fluid to remove during a given treatment session. The amount of fluid to be removed is determined before the treatment session and is related to the patient's pre-treatment weight, fluid addition during treatment and their theoretical dry weight. However, it can be difficult to accurately determine a patient's dry weight, which is considered to be the weight that the person would be if their kidneys were properly functioning. What a given patient might weigh if their kidneys were properly functioning is often an unknown variable and can change over time. Yet an accurate determination of the patient's dry weight is important to the successful outcome of a fluid removal session.

Unfortunately, the patient's dry weight is not typically calculated or re-evaluated frequently. Unlike the patient's actual weight, which is measured before and after a fluid removal session, dry weight is often determined much less frequently; e.g. monthly, and much can change in the time between a dry weight determination and a given fluid removal session, which typically occurs three times a week. While being an important variable in fluid removal considerations, dry weight is often difficult to calculate and may vary between sessions.

Errors in fluid volume removal can result in severe hypotension and patient crashing following or during hemodialysis treatment, and insufficient frequency of fluid removal sessions can have serious consequences. For example, sudden and cardiac death (including death from congestive heart failure, myocardial infarction, and sudden death) are common in hemodialysis patients. See Bleyer et al, "Sudden and cardiac death rated in hemodialysis patients," *Kidney International*, (1999), 55:1552-1559.

For various reasons, additional monitoring of patients for which a blood fluid removal session is indicated may be desired.

SUMMARY

This disclosure, among other things, describes devices, systems and methods for chronically monitoring fluid volume of patients undergoing or suspected of needing to undergo fluid removal procedures, such as hemodialysis, ultrafiltration, or the like. By chronically monitoring indicators of fluid volume, it may be possible to more accurately predict when stage 3 or stage 4 chronic kidney disease patients may first require supplemental fluid removal treatment, potentially allowing for better predictions as to when a fistula should be initiated so that it is mature by the time of the first fluid removal session. Chronic monitoring of indicators of fluid volume may also be valuable in more accurately identifying appropriate fluid removal parameters (fluid removal "prescription") for use during fluid removal sessions.

In any embodiment, a method can comprise monitoring an indicator of fluid volume of a patient with an implantable sensor, and setting an initial fluid volume prescription for a blood fluid removal session based on the monitored indicator of fluid volume.

In any embodiment, the method can comprise transmitting data regarding the indicator of fluid volume from the implantable sensor device to a fluid removal device.

In any embodiment of the method, setting the initial fluid volume removal prescription can comprise calculating the fluid volume prescription by the fluid removal device based on the data received from the implantable sensor.

In any embodiment, the fluid removal device can be wearable.

In any embodiment, the fluid removal device can be implantable.

In any embodiment of the method, the indicator of fluid volume can be an indicator of tissue fluid volume or an indicator of blood fluid volume.

In any embodiment of the method, the indicator of fluid volume can be tissue impedance or blood hematocrit.

In any embodiment, the method can comprise determining whether the indicator of tissue fluid volume crosses a predetermined threshold value, and providing an alert to the patient if the indicator of fluid volume is determined to cross the threshold value.

In any embodiment, monitoring the indicator of fluid volume can comprise monitoring an indicator of tissue fluid volume, the method can further comprise monitoring an indicator of blood fluid volume, and setting the initial fluid volume removal prescription for the blood fluid removal session based on the monitored indicator of fluid volume can comprise setting the initial fluid volume removal prescription based on the ratio of the monitored indicators of tissue fluid volume and blood fluid volume.

In any embodiment, monitoring the indicator of fluid volume can comprise monitoring an indicator of blood fluid volume, the method can further comprise monitoring an indicator of tissue fluid volume, and setting the initial fluid volume removal prescription for the blood fluid removal session can comprise setting the initial fluid volume removal prescription based on the ratio of the monitored indicators of tissue fluid volume and blood fluid volume.

In any embodiment, the method can comprise determining whether the monitored indicator of fluid volume crosses a predetermined threshold; and providing a sensory cue to the patient if the monitored indicator is determined to cross the threshold.

In any embodiment, the sensor device can comprise a detector circuit and components configured to acquire sensed data regarding an indicator of fluid volume; and control electronics configured to receive the acquired sensed data from the detector circuit and to calculate a fluid volume removal prescription based on the acquired sensed data.

In any embodiment of the method, the control electronics can comprise a computer readable medium that, when implemented, cause the electronics to calculate the initial fluid rate removal prescription based on data received from the sensor and instruct the fluid rate removal controller to operate according to the initial fluid rate removal prescription.

In any embodiment of the method, the indicator of fluid volume can be an indicator of interstitial fluid volume.

In any embodiment of the method, setting an initial fluid volume removal prescription can comprise a setting a volume rate of a replacement fluid that is added to a patient's blood.

In any embodiment, the method can comprise setting an initial fluid rate removal prescription for the blood fluid removal session based on the monitored indicator of fluid volume.

In any embodiment, setting the initial fluid rate removal prescription can comprise calculating the fluid rate removal prescription by a fluid removal device based on the data received from the implantable sensor.

In any embodiment, the sensor can be configured to measure tissue impedance at a first location; and the method can comprise measuring tissue impedance at a second location; and determining whether the impedance measured at the first location and the impedance measured at the second location differ by a predetermined amount.

In various embodiments described herein, a sensor device can comprise a detector circuit and components configured to acquire sensed data regarding an indicator of fluid volume; and control electronics configured to receive the acquired sensed data from the detector circuit and to calculate a fluid volume removal prescription based on the acquired sensed data. In any embodiment, the sensor device can be configured to carry out any of the methods described herein.

In various embodiments described herein, a method includes monitoring an indicator of fluid volume of a patient via a sensor device, and setting an initial fluid volume removal prescription for a blood fluid removal session based on the monitored indicator of fluid volume. The method may further include transmitting data regarding the indicator of fluid volume from the implantable sensor device to fluid removal device. In some embodiments, the fluid removal device sets or calculates the initial fluid volume removal prescription based on the data received from the implantable sensor. The indicator of fluid volume may be an indicator of tissue fluid volume or an indicator of blood fluid volume.

In some embodiments described herein, a system includes a sensor configured to monitor an indicator of fluid volume and a blood fluid removal device. The blood fluid removal device includes (i) an inlet for receiving blood from a patient, (ii) an first outlet for returning blood from the patient, (iii) a medium for removing fluid from the blood, the medium being positioned between the inlet and the first outlet, (iv) a fluid rate removal controller, (v) a second outlet for flow of the removed fluid, and (vi) electronics coupled to the fluid rate removal controller and the sensor, wherein the electronics are configured to set an initial fluid rate removal prescription based on data received from the sensor and to control the fluid rate removal controller based on the set initial fluid rate removal prescription. In numerous embodiments described herein, a sensor device includes (i) a detector circuit and components configured to acquire sensed data regarding an indicator of fluid volume; and (ii) control electronic configured to receive the acquired sensed data from the detector circuit and to calculate a fluid volume removal prescription based on the acquired sensed data.

The devices and methods used herein with regard to chronic monitoring of an indicator of fluid volume may also be used to assist in determining an appropriate time for creating a fistula in a patient suffering from or at risk of chronic kidney disease.

One or more embodiments of the systems, devices and methods described herein may provide one or more advantages over prior systems, devices and methods for blood fluid removal in patients or monitoring fluid in patients. For example, chronic kidney disease patients are often are not aware of their disease until it is too late (Stage 5). When patients reach stage 5, treatment options are limited and hemodialysis is often the only option. If monitoring can help patients to track their kidney functions (especially for those with hypertension and diabetes), the patients may be treated with therapies other then dialysis and their progress toward stage 5 may be slowed. In cases where patients are treated with diuretic therapy, monitoring can be used to track whether patients respond to the treatment. Monitoring may also help to avoid misdiagnosis. For example, patients with kidney disease may be diagnosed as merely hypertensive without regard to impaired renal function, thereby missing an opportunity to slow the progression of chronic kidney disease. For patients with hypertension and diabetes, monitoring as described herein may be valuable, as hypertension and diabetes are thought to contribute to ⅔ of the stage 5 kidney failure patients. These advantages and others will be apparent to those of skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
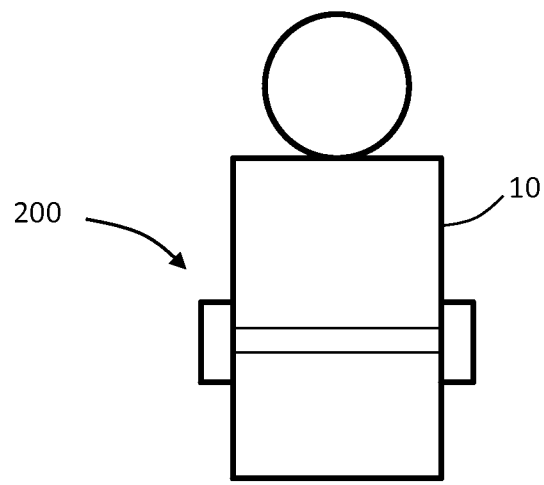
FIGS. 1-2 are schematic diagrams showing wearable (FIG. 1) and implantable (FIG. 2) sensors in relation to a patient.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, "chronic" with regard to monitoring, means that monitoring occurs over the course of days, weeks, months or years. The chronic monitoring may include continuous, periodic, intermittent, or the like sensing over the time frame that monitoring occurs.

As used herein, "fluid volume" may refer to tissue fluid volume or blood fluid volume.

As used herein, "tissue fluid volume" means the volume of fluid (as opposed to cells or solids) in a tissue or region of a patient, which can be the entire patient. Tissue "fluid" is often referred to as interstitial fluid. In various embodiments, one or more of tissue fluid volume, rate of change of tissue fluid volume, or the like, or indicators thereof, are monitored in accordance with the teaching presented herein.

As used herein, "blood fluid volume" means the volume or percentage of blood volume that is occupied by fluid, as opposed to cells or solids in the blood. In various embodiments, one or more of blood fluid volume, rate of change of blood fluid volume, or the like, or indicators thereof, are monitored in accordance with the teaching presented herein.

As used herein, a "blood fluid removal process," or the like, refers to a process from which fluid is removed from blood of a patient and the blood is returned to the patient. In most cases, the blood is also cleaned; i.e., waste products are removed from the blood and cleaned blood is returned to the patient. Examples of blood fluid removal processes include ultrafiltration, hemofiltration, hemodialysis, hemodiafiltration, peritoneal dialysis and the like. Any patient for which blood fluid removal is indicated may benefit from the devices, systems and methods described herein.

As used herein, a "patient for which a blood fluid removal session is indicated" is a patient that has undergone, is undergoing, or is likely to undergo at least one blood fluid removal session. In general, such patients are fluid overloaded patients, such as patients suffering from heart failure, chronic kidney disease, or acute kidney failure. Often such patients are stage 3 to stage 5 chronic kidney disease patients, are unresponsive or under-responsive to diuretics, or the like.

This disclosure, among other things, describes devices, systems and methods for chronic monitoring fluid volume of patients undergoing or suspected of needing to undergo fluid removal procedures, such as hemodialysis, ultrafiltration, or the like. The chronic monitoring may improve the treatment or outcomes of such patients by providing indications of when therapeutic intervention may be indicated or by facilitating an appropriate determination of the amount and rate of fluid removal to be removed during a particular treatment session. Any suitable monitoring or sensor device may be used.

Figure 2:
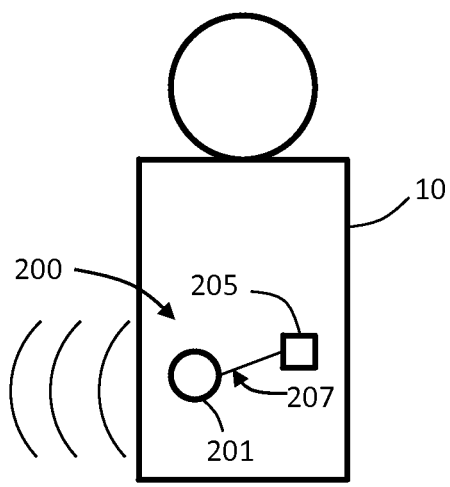

In some embodiments and with reference to FIGS. 1-2, sensor 200 for chronic monitoring, or components thereof are wearable (FIG. 1) or implantable (FIG. 2). In the embodiments shown in FIG. 1, sensor 200 is shown as a belt-like device worn around patient's 10 waist. Of course, sensor 200 or components thereof may be configured to be worn on any suitable portion of a patient's 10 body. For example, the sensor 200 apparatus may be configured to work around a wrist or ankle, attached to a finger or toe, or the like. In the embodiment depicted in FIG. 2, the sensor 200 and components 201, 205, 207 thereof are implanted in patient's 10 abdominal region. Of course, the sensor 200 or components 201, 205, 207 thereof may be implanted in any suitable region that are practicable from a patient comfort stand point, as well as a technical standpoint for purposes of sensor function. As shown in FIG. 2, the implantable sensor 200 is preferably configured to communicate (e.g., wirelessly) with devices outside of patient's 10 body or other implanted devices.

Whether the sensor 200 is wearable or implantable, it is preferred that the sensor 200 include a power source that enables a patient to carry about their daily activities without having to plug the sensor 200 into an electrical outlet. Examples of suitable power sources include a battery, which may be rechargeable, a coupled capacitor, or the like.

Figure 3:
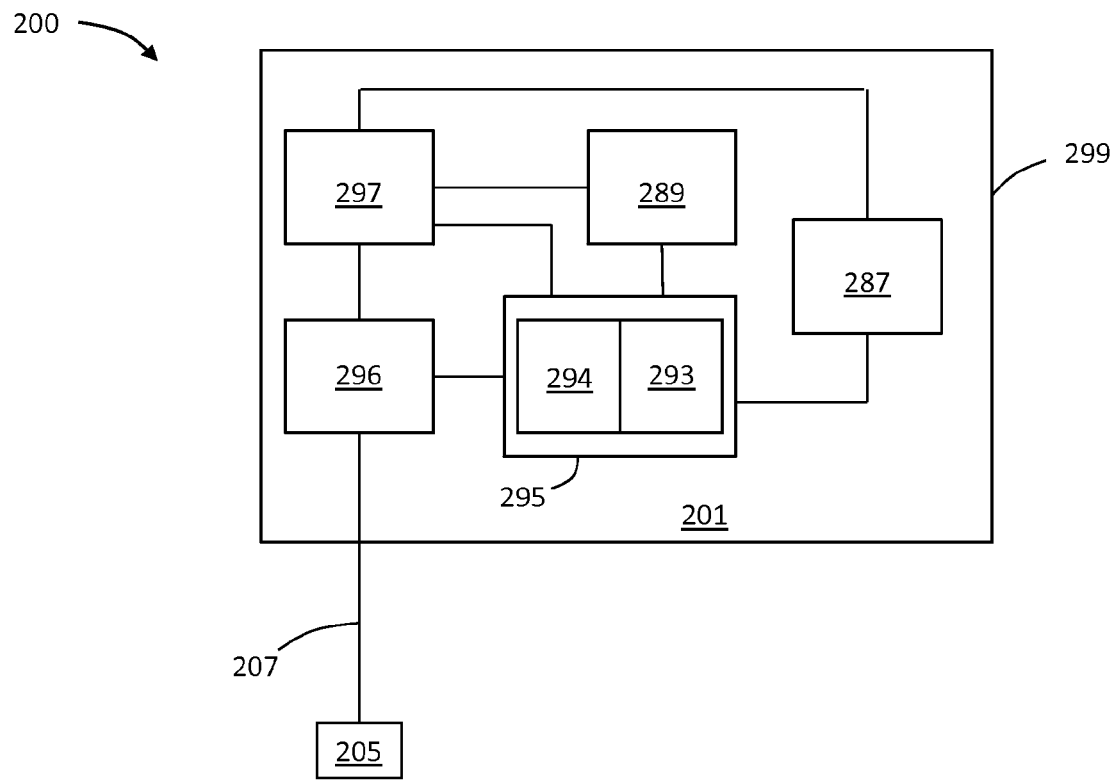
FIG. 3 is a schematic block diagram showing selected components of a sensor.

For purposes of illustration, a block diagram of selected components of an implantable sensing device 200 is shown in FIG. 3. The depicted sensing device 200 has a housing 299 containing a number of components, including power source 297, control electronics 295, detector circuit 296, indicator circuit 287, and telemetry circuit 289. In the depicted embodiment, the detector circuit 296, which may include and analog-to-digital convertor, a band-pass filter, or the like, is operably coupled to a detector 205, which may be located outside of housing 299 and coupled to detector circuit 296 via an electrical lead 207. Detector circuit 296 is operably coupled to power source 297 and control electronics 295, which include a processor 294 and a memory 293 for storing acquired sensed data and processor instructions. Control electronics are also operably coupled to power source 297, which may be a battery or the like, and to telemetry circuitry 289 for wirelessly communicating with a device external to the patent or with other implanted devices. The telemetry circuit 296 allows the sensor device 200 to transmit data regarding a monitored indicator of fluid volume to another device. Telemetry circuit 296 may include a telemetry antenna or other suitable components for transmitting or receiving data, as well-known in the art. Indicator circuit 287 is operably coupled to power supply 297 and control electronics 295, which may activate indictor circuit 287 to provide a sensory cue when a fluid volume is approaching a level for therapeutic intervention is warranted. Indicator circuit 287 may include microspeakers for providing an audible signal or a vibration mechanism for alerting the patient. For example, if fluid volumes are determined to exceed a threshold or if the rate of increase in fluid volume exceeds a threshold, the patient may be alerted that therapeutic intervention may be needed. It will be understood that the sensor 200 may include components other than those depicted, as are generally known in the art. In some embodiments, sensor 200, via telemetry circuit 287, alerts a healthcare provided if a threshold is exceeded by transmitting to a patient programmer, patient controller, hand-held device, phone, remote desktop device (e.g., computer, bedside monitor, table-top monitor), or the like. The information may pass from any of these devices via a network (wireless, cellular, wired, etc.) to be accessible to a healthcare provider.

It will also be understood that a wearable sensing device may have similar components or may be configured differently. For example, a communication circuit for wired communication may replace, or be present in addition to, a telemetry circuit.

In various embodiments, a sensor for chronic fluid monitoring may be used to monitor blood fluid volume, or an indicator thereof. Typically, the sensors measure fluid volume indirectly, and thus directly monitor an indicator of fluid volume. For example, in some embodiments, sensor indirectly monitors hematocrit (the portion of blood volume that is occupied by red blood cells). Any suitable hematocrit sensor, such as a CRIT-LINE monitor from HEMA METRICS (see, HEMA METRICS, CRIT-LINE hematocrit accuracy, Vol. 1, Techn Note No. 11 (Rev. D) Feb. 24, 2003), may be used or modified for use in devices and methods described and contemplated herein. A typical hematocrit level for a healthy adult male is between about 40% and 54% or about 47%, and a typical level for a healthy adult female is between about 37% and 47%, or about 42%. As the state of renal disease progresses in a patient, or prior to a blood fluid removal session, the fluid volume of the patient may be elevated, thus hematocrit levels may be lower than desired.

Hematocrit levels, or an approximation or indicator of hematocrit levels, can thus be used to monitor blood fluid volume. In some embodiments, hemoglobin levels are monitored as an indicator of hematocrit levels and blood fluid volume, as hemoglobin concentration is typically proportional to red blood cell concentration. Any suitable sensor may be used to measure hemoglobin concentration, such as sensors used in pulse oximeters which measure adsorption of red and infrared light to determine concentration of oxygenated hemoglobin and deoxyhemoglobin, respectfully. In some embodiments, the sensor may be clipped to a patient's finger and may employ pulse oximeter technology for detecting hemoglobin levels as an indicator of blood fluid volume. Of course, the sensors (which may include the associated light source(s)) may be placed in any suitable location, such as around tubing that carries blood from the patient to the blood fluid removal device or from the blood fluid removal device to the patient, within the blood fluid removal device, or the like. In some embodiments, the sensor is implanted in a patient and disposed about a blood vessel to measure hemoglobin levels, and thus hematocrit and blood fluid levels.

Figure 4:
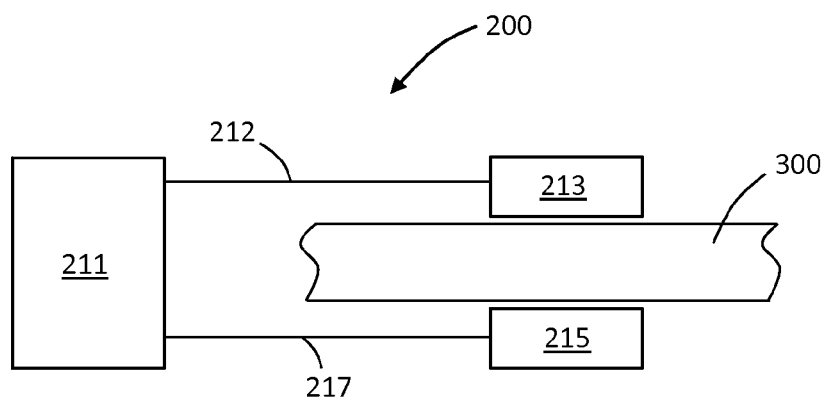
FIG. 4 is a schematic block diagram of selected components of a sensor for monitoring an indicator of blood fluid volume in relation to tubing.

By way of example and with reference to FIG. 4, a schematic diagram of a sensor 200 and tubing 300, which may be a blood vessel, are shown. A light source 213 of appropriate wavelength (red or infrared) is positioned on one side of tubing 300 such that the light passing through tubing 300 hits detector 215. More light is absorbed (and less hits the detector 215) if a higher concentration of hemoglobin is present in tubing 300. A lead 212 carries power and other electrical signals, if appropriate, to the light source 213 from the sensor device body 211, which may contain the power source and other control or detecting electronics. Lead 217 carries electrical signals from detector 215 to the components housed in sensor device body 211.

Regardless of the placement of the sensor 200, the sensor may be calibrated by monitoring flow of blood having known hematocrit levels through tubing 300 (whether a blood vessel or tubing for use with a blood fluid removal device). The values obtained may be stored in a lookup table for reference during a blood fluid removal session or as otherwise needed while the sensor is in use. In some embodiments, the reference signal may be reset or obtained after a blood fluid cleaning session when the patient's blood should be at its desired fluid level. In some embodiments, the rate of change of blood fluid volume may be determined by comparing the rate of change in light absorbance; e.g., as the blood fluid volume increases following a blood fluid cleaning session or as the patient's condition worsens.

The discussion above with regard to hemoglobin sensing is provided as an example of how known sensing technologies and components may be employed in accordance with the teachings presented herein with regard to blood fluid volume monitoring. It will be understood that other technologies and components may be used to monitor blood fluid volume. For example, total blood protein or albumin concentrations and blood pressure, alone or in combination, can be used to evaluate blood volume. By way of example, high blood pressure combined with low hematocrit or low blood protein indicates a higher possibility of blood fluid overloading. Alternatively or additionally, blood viscosity may be used as an indicator of blood fluid volume and may be measured by pressure or flow.

Figure 5:
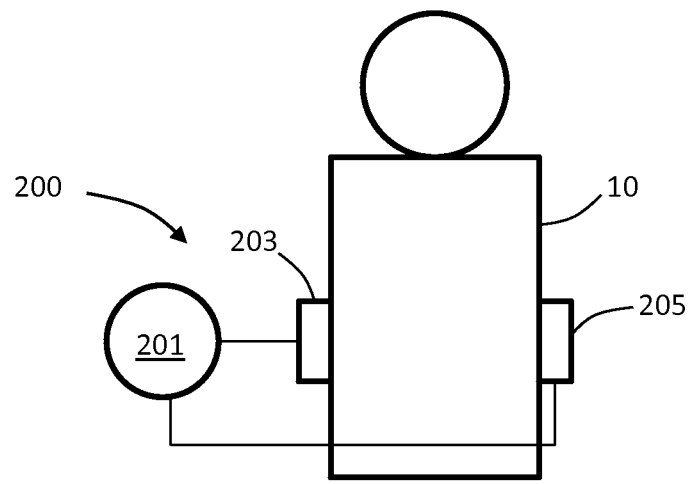
FIGS. 5-6 are schematic block diagrams of selected components of impedance sensors, external to (FIG. 5) and implanted in (FIG. 6) a patient.
Figure 6:
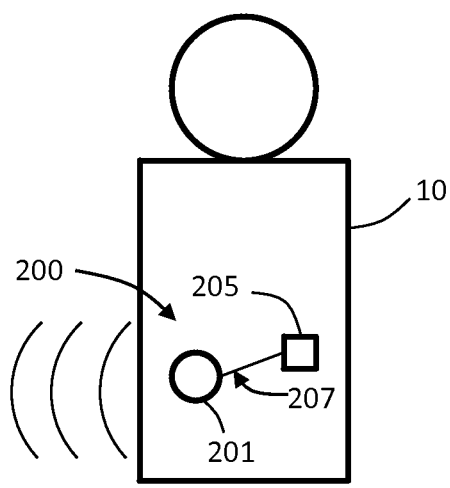

In various embodiments, a sensor for chronic fluid monitoring may be used to monitor tissue fluid volume, or an indicator thereof. Any suitable sensor may be employed. By way of example, impedance of flow of current through a tissue of a patient may be monitored as an indicator of fluid volume in the tissue. With reference to FIGS. 5-6, the impedance sensor 200 may be external (FIG. 5) or implantable (FIG. 6). As fluid volume rises in the tissue, impedance is decreased. It will be understood that capacitance, dielectric constant, and other similar measures may also be used, as these are correlated to fluid volume, and further impedance. For the purposes of this disclosure, monitoring of electrical properties of a tissue that are correlated to impedance is considered to be subsumed under the definition of monitoring "impedance."

As depicted in FIG. 5, impedance may be monitored between two electrodes 203, 205. The electrodes 203, 205 are operably coupled to control and processing electronics 201 via leads. The electronics 201 are configured to generate a voltage differential between the electrodes 203, 205, current may be measured and impedance calculated. The measurement may be done in either DC or AC mode. Impedance or phase angle may be correlated to tissue fluid volume. Suitable external impedance monitors 200 and components that may be used in accordance with the teachings described herein are known and described in the art.

In the example depicted in FIG. 6, a conductive housing containing control electronics 201 serves as a reference electrode to electrode 205. Impedance is monitored in the tissue between the housing and the electrode 205. The electrode 205 is coupled to the control electronics 210 via lead 207. As depicted in FIG. 6, the control electronics 201 are configured to wirelessly communicate with a device external to the patient for purposes of transmitting data regarding monitored impedance.

Tissue impedance sensing for purposes of monitoring tissue fluid volume has been well documented. One example of a well studied system that may be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., (i) Siegenthalar, et al. Journal of Clinical Monitoring and Computing (2010): 24:449-451, and (ii) Wang, Am. J. Cardiology, 99(Suppl):3G-1-G, May 21, 2007. Alternatively or in addition, tissue impedance may be monitored for a suitable period of time to establish as suitable baseline, and patient markers or clinician input may be used to instruct whether the patient is fluid overloaded or under-loaded. The data acquired by impedance sensor and input data regarding fluid status of the patient at the time the sensor data is acquired may be used to establish suitable ranges for impedance values.

In some embodiments, more than one implanted impedance sensor, such as more than one OptiVol® fluid status monitoring system, may be employed. The sensors may be configured or placed to monitor impedance of different tissues, different areas of the same tissue, or the like. Duplication of sensors may provide redundancy in case of sensor failure or as a check on the readings obtained from another sensor. In some cases, tissue fluid changes detected by a sensor may be due to conditions other than chronic heart failure or renal disease. For example, increased lung fluid may result from pneumonia. Such fluid may not be indicative of a need for a blood fluid removal session. By having a second impedance sensor placed to monitor, e.g., abdominal fluid, a check may be placed on the sensor placed and configured to monitor lung fluid volume. The sensors may be configured to communicate with each other or another device to determine whether the sensor readings are significantly different or whether the difference exceeds a threshold value, in which case the patient may be prompted to seek medical attention. The use of more than one impedance sensor should be valuable in reducing the likelihood of false positive or false negative fluid overload conditions.

The discussion above with regard to impedance monitoring is provided as an example of how known sensing technologies and components may be employed in accordance with the teachings presented herein with regard to tissue fluid volume monitoring. It will be understood that other technologies and components may be used to monitor tissue fluid volume. For example, the concentration of an electrolyte, such as sodium, potassium, or calcium may be measured in a tissue using an ion selective electrode, with concentrations being higher with lower tissue fluid volume. By way of further example, a pressure sensor may be placed in the tissue to measure extension or contraction of tissue as fluid volume changes, stress and strain sensors may be used to measure modulus or stress-strain curves for tissue and may be used to correlate to different tissue fluid volumes, stress relaxation or creep profiled of tissue may be measured and correlated with different fluid volumes, etc. Another example of indirect tissue fluid monitoring is a measure of lung noise, which tends to be greater during fluid overload due to impedance of air flow.

Regardless of the sensor or sensor configuration employed and regardless of whether the sensor is configured to monitor blood fluid or tissue fluid, the sensor data may be used to improve treatment or outcomes of fluid overloaded patients such as patients suffering from chronic kidney disease. In various embodiments, the sensor data may be used to assist in determining the timing of the creation of a fistula. In some embodiments, the sensor data may be used to aid in determining an appropriate fluid volume removal prescription (e.g., amount and rate or profile of fluid removal) of a blood fluid removal session. In some embodiments, the sensor data may be used during a blood fluid removal treatment session, e.g. as described in U.S. provisional patent application No. 61/480,528, filed on the same date as the present disclosure, entitled FLUID VOLUME MONITORING FOR PATIENTS WITH RENAL DISEASE, which provisional patent application is hereby incorporated herein by reference in its entirety to the extent that it does not conflict with the disclosure presented herein.

Figure 7:
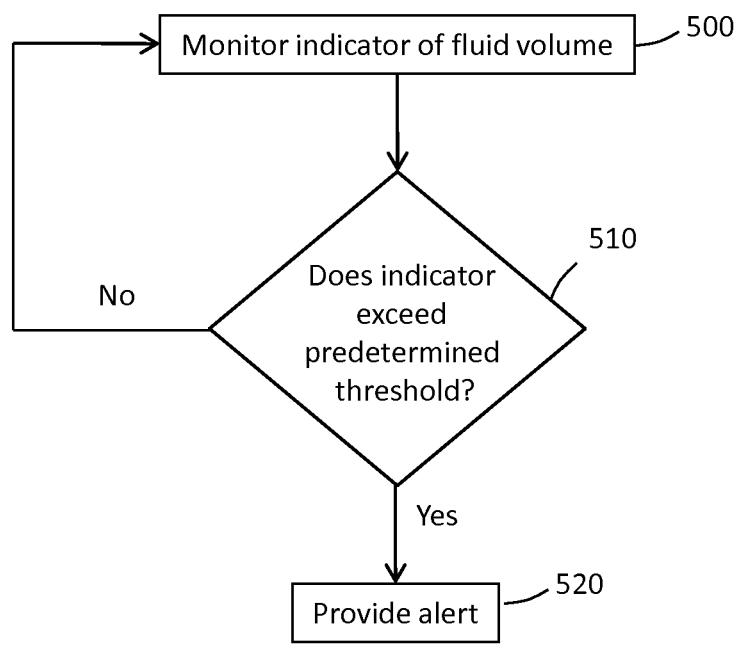
FIGS. 7-9 are flow diagrams depicting overviews of methods in accordance with various embodiments described herein.
Figure 8:
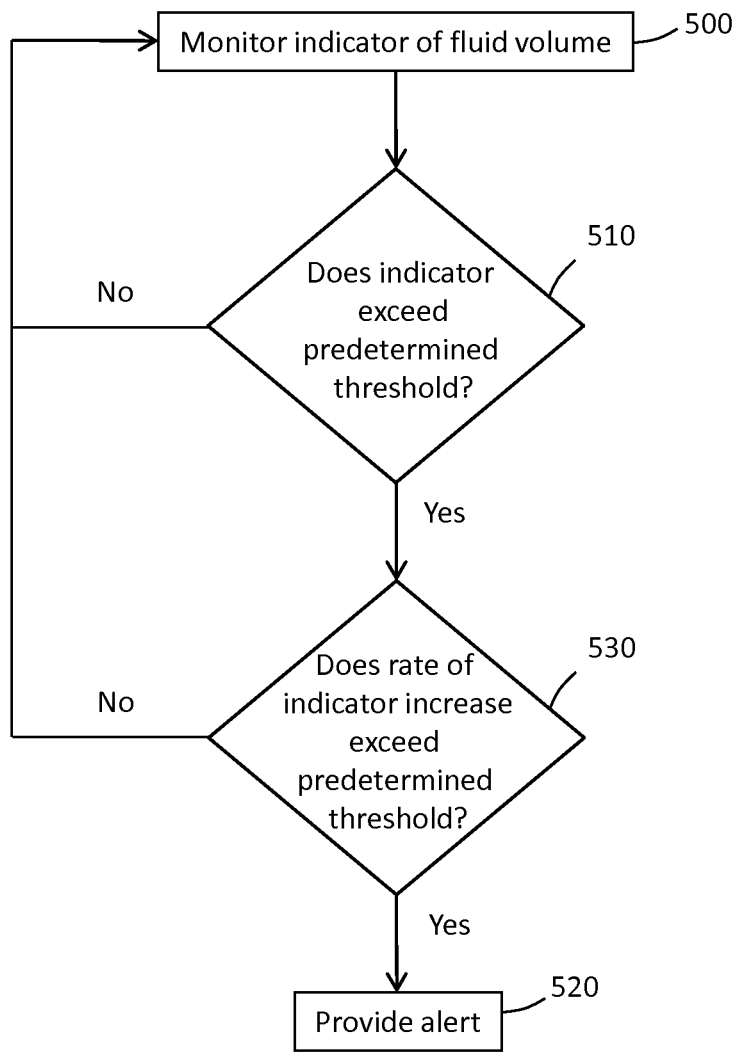
Figure 9:
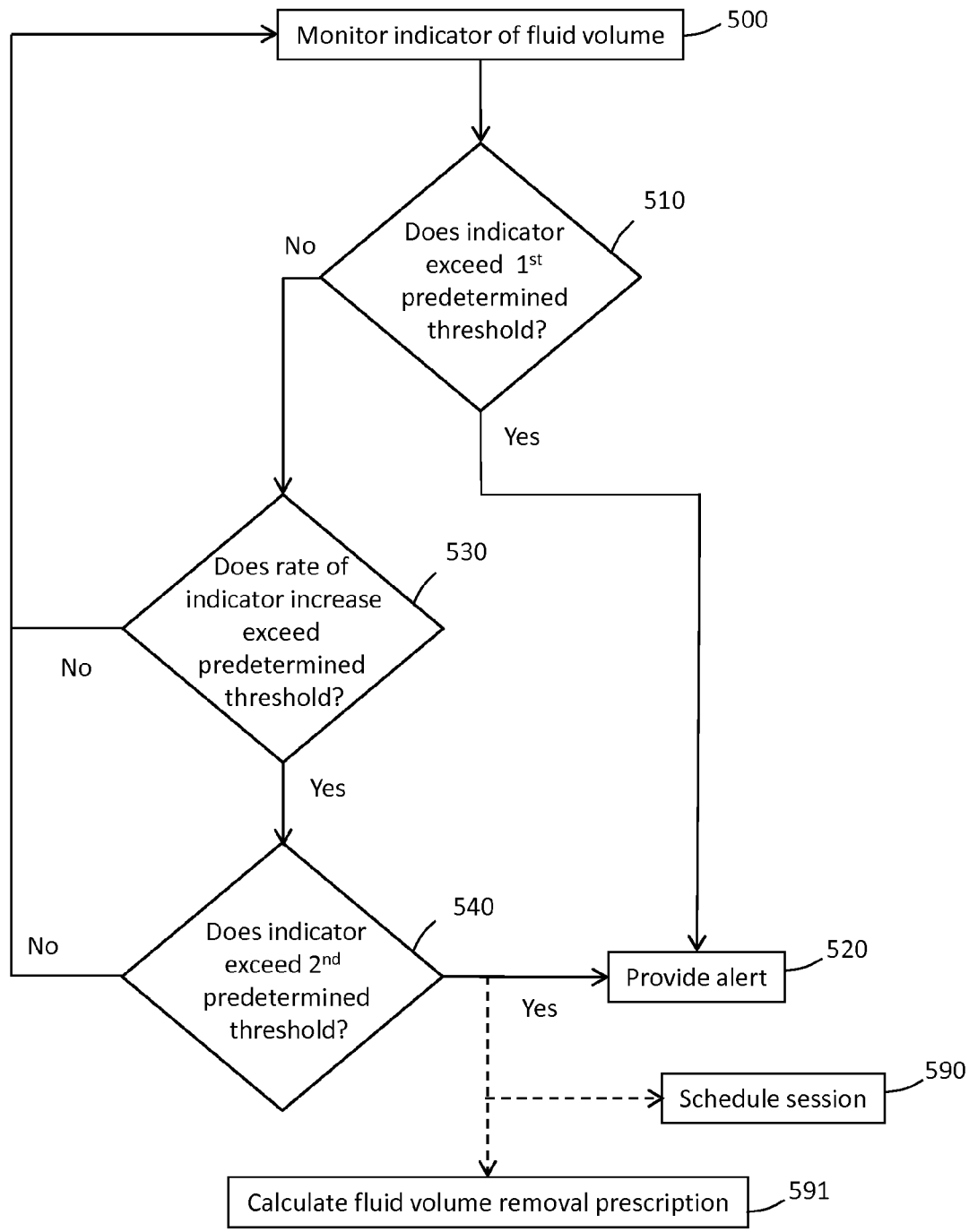

Referring now to FIGS. 7-9, overviews of embodiments of methods for chronic monitoring of fluid volume is presented. In some embodiments, the methods may be used for purposes of assisting in determining the appropriate timing of a creation of a fistula. For example, an indicator of fluid volume (e.g., as discussed above) may be monitored (500) and a determination may be made as to whether the indicator exceeds a predetermined threshold (510), such as a threshold that is indicative of excess fluid levels that would warrant creation of a fistula. The threshold may be based on empirical data collected over populations of patients based on closely monitored patients in accordance with existing medical practice, may be based on changes from baseline within a given patient, or the like. If the monitored indicator exceeds a threshold indicative of increased fluid, an alert may be provided (520), such as an alert provided by an indicator circuit of a sensor as described above. The sensor may also schedule an appointment with a healthcare provider or may store and transmit data regarding the monitored indicator of fluid volume to a healthcare provider via an external device, such as a programmer, a computer, a personal data assistance, a tablet or the like.

In some embodiments, the methods depicted in FIGS. 7-9 may used for determining whether a heart failure patient is close to decompensating. Data regarding fluid levels before or during the patient's prior decompensation events may be marked or evaluated. By way of example, a physician or health care provide may interrogate a fluid monitoring device to better understand events that preceded a patient's visit when presenting with heart failure decompensation. Thresholds for alerts may be adjusted based on monitored fluid levels, rates, etc. that occurred prior to the patient's visit. In some embodiments, the monitoring device or system including the monitoring device may receive input regarding the patient's decompensation status, and the device or system may be reviewed data stored in memory to determine whether certain patterns appear in relation to decompensation. Thresholds for issuance of alerts may be adjusted automatically by the device or system.

As shown in FIG. 8, a method may include determining whether the rate of fluid increase, based on the monitored indicator, exceeds a predetermined threshold (530). If the rate of increase of fluid volume is high or exceeds a threshold, the alert (etc.) may be provided. In some embodiments, it may be desirable to determine whether the rate exceeds a threshold (530) prior to determining whether the overall value of the indicator exceeds a threshold (510), because if the rate of increase is high, the overall threshold may be lower than if the rate is low. That is, the threshold (510) may be based on the rate (530).

For example and as shown in FIG. 9, a method may include determining whether the monitored indicator exceeds a first high threshold (510), in which case an alert (etc.) is provided (520). If the indicator does not exceed the first high threshold (510), a determination may be made as to whether the rate of increase of fluid, as indicated by the sensed data, exceeds a threshold (530). If the rate of increase exceeds a threshold, a determination may be made as to whether the value of the monitored indicator (as it is indicative of fluid volume) exceeds a lower second threshold (540). In which case, the alert (etc.) may be provided (520). In this way, a lower threshold may be set if the rate of increase is high. The threshold values may be entered into lookup tables based on prior data from other patients or populations or may be "learned" based on sensed data acquired within the patient.

It will be understood that the methods depicted in, and described with regard to FIGS. 7-9, may be useful for patients that are already undergoing blood fluid removal treatments, and may be used for purposes of automatically scheduling fluid removal session (e.g., 590, FIG. 9), e.g., via telemetry circuit as described above. A sensor monitoring the indicator of fluid volume may also calculate a fluid volume prescription based on the sensed data (e.g., 591, FIG. 9) and transmit data regarding the prescription to a fluid volume removal device or other device that will allow a healthcare provider to enter the appropriate fluid volume removal prescription. Alternatively or in addition, data regarding the monitored indicator may be sent to a fluid volume removal device or other device, which may then calculate an appropriate fluid volume removal prescription (e.g., 591, FIG. 9) based on the transmitted data. The fluid volume prescription data calculated by the sensor device or other device may be based on prior data from other patients or populations or may be "learned" based on sensed data acquired within the patient over time.

Any suitable device or system for removing fluid, or fluid and contaminants, from blood may be used in accordance with the teachings presented herein. The devices, or components thereof, may be traditional large counsel-type, wearable, implantable, or the like.

Figure 10:
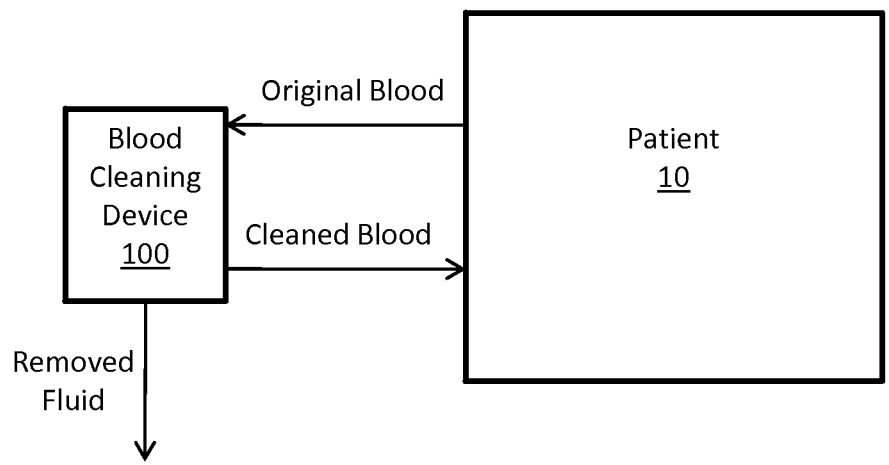
FIGS. 10-13 are schematic block diagrams of embodiments of fluid removal devices that may be employed in accordance with the teaching presented herein.

Block diagrams of some examples devices and systems for blood fluid removal are shown in FIGS. 1-4. As shown in FIG. 10, blood may be removed from a patient 10 and fluid may be removed via a blood fluid removal device 100 and returned to the patient 10. Removed fluid may be diverted. In some embodiments where the blood fluid removal device 100 or system, or components thereof, are implanted, the removed fluid may be diverted to the patient's bladder. Examples of blood fluid removal devices 100 that may operate as depicted in FIG. 10 are ultrafiltration and hemofiltration devices. Examples of such devices and components thereof that may be employed in accordance with the teachings presented herein are well known in the art. It will be understood that peritoneal dialysis, where dialysate is introduced into the peritoneal cavity, may also be employed.

Figure 11:
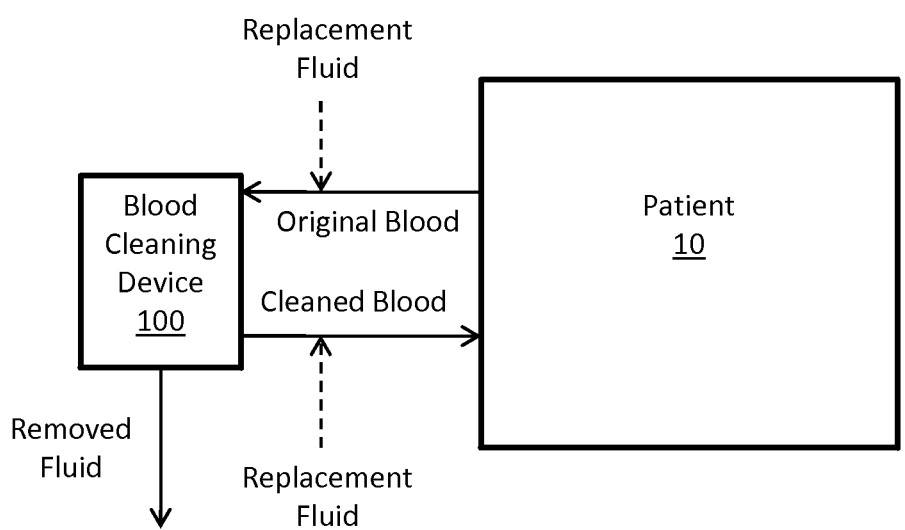

With some of such devices, fluid may be removed at too great of a rate. Accordingly and with reference to FIG. 11, replacement fluid may be introduced into the patient's blood. As shown in FIG. 11, the replacement fluid may be added to the original blood before fluid removal or may be added to the blood after initial fluid removal and prior to return to the patient's cardiovascular system. Preferably, the replacement fluid is added after initial fluid removal.

Figure 12:
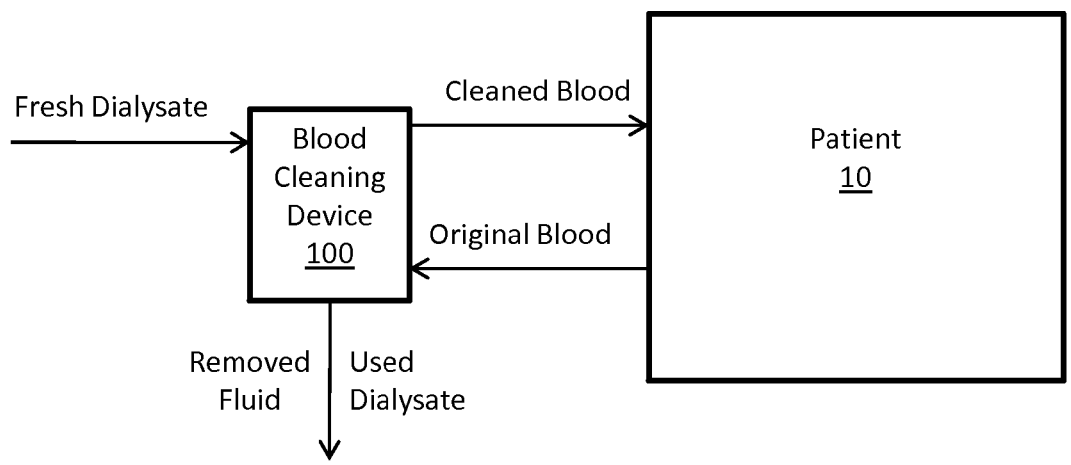

As shown in the embodiment depicted in FIG. 12, the blood fluid removal device 100 may employ dialysate to assist in removal of contaminants from the patient's blood and in maintaining proper pH and electrolyte balance. Used dialysate and fluid removed from the blood may be diverted. In some embodiments, particularly where the blood fluid removal device 100 or system or components thereof are wearable or implantable, the used dialysate and removed fluid, or a portion thereof, may be regenerated to produce fresh dialysate for re-use in the blood fluid removal process. One system for regeneration of dialysate is the REDY system, such as described in Roberts, M, "The regenerative dialysis (REDY) sorbent system," *Nephrology* 4:275-278, 1998, which system may be employed or readily modified for use in embodiments described herein. Systems and devices that operate in a manner shown in the embodiment of FIG. 12 include hemodialysis and hemodiafiltration systems. Examples of such devices and components thereof that may be employed in accordance with the teachings presented herein are well known in the art.

Figure 13:
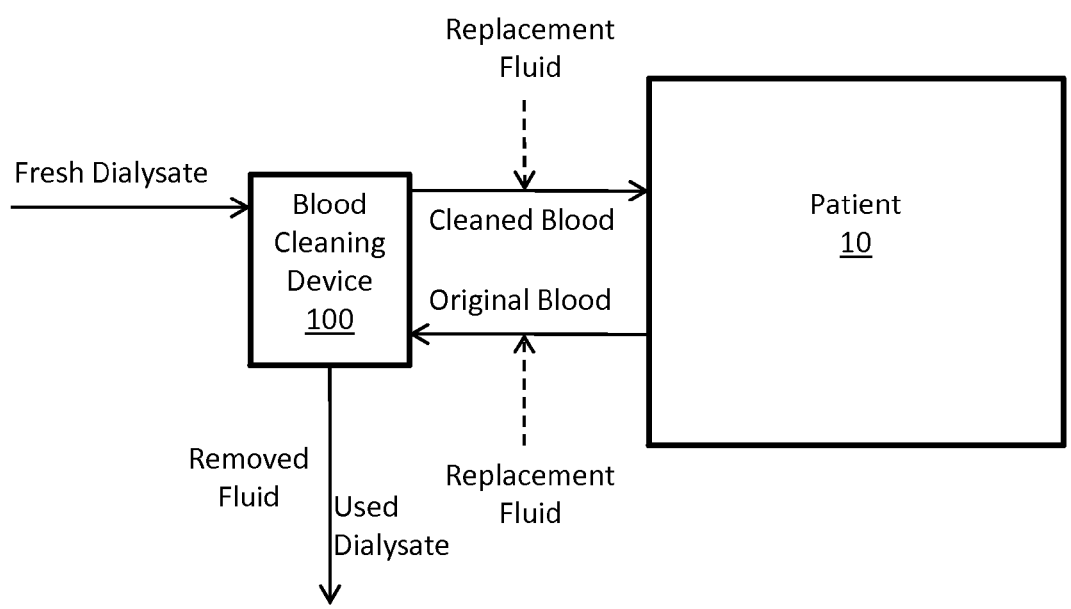

As shown in FIG. 13, in cases where the blood fluid removal device 100 of FIG. 12 removes fluid from the blood at too high of a rate, replacement fluid may be introduced into the patient's blood, upstream or downstream of fluid removal.

Regardless of the device or blood fluid removal process employed, it is important to control the amount and rate of fluid removal to avoid severe hypotension, heart failure or sudden cardiac death in patients from whom blood fluid is removed. It is also important to control the amount and rate of fluid removal for purposes of efficiency. That is, even though it may be generally safer to remove fluid very slowly, such slow removal may result in blood fluid removal sessions that last for considerable periods of time. While such slow removal may be acceptable for blood fluid removal systems that are wearable or implantable, it may not be acceptable for larger stand alone systems that require a patient visit to a clinic. The patient's quality of life, which is typically already low, may suffer from extended stays in the clinic that would be necessary for systems that slowly remove fluid from the blood. Ideally a blood fluid removal device or system balances the health concerns with the efficiency concerns in controlling the rate of fluid removal.

Of course, the amount of fluid removed is also an important variable in maintenance of patient health. If too little fluid is removed, the patient is burdened with excess fluid, which can lead to heart failure, hypertension, or other disorders, until their next blood fluid removal session or until their fluid removal prescription is changed. If too much fluid is removed, the patient may suffer from hypotension, crashing, sudden cardiac death, or the like. Accordingly, it would be desirable to remove fluid from the blood not only at an acceptable rate, but also in an acceptable amount.

The data acquired from sensors, e.g. as described above, used in chronic monitoring of indicators of fluid volume may, in some embodiments, be used to allow initial fluid volume removal prescriptions to be more accurate and reliable than those currently used based on dry weight (which often may be determined days or weeks from a given fluid removal session). In some embodiments, the sensor data may be used during a blood fluid removal treatment session, e.g. as described in U.S. provisional patent application No. 61/480,528, filed on the same date as the present disclosure, entitled FLUID VOLUME MONITORING FOR PATIENTS WITH RENAL DISEASE.

Figure 14:
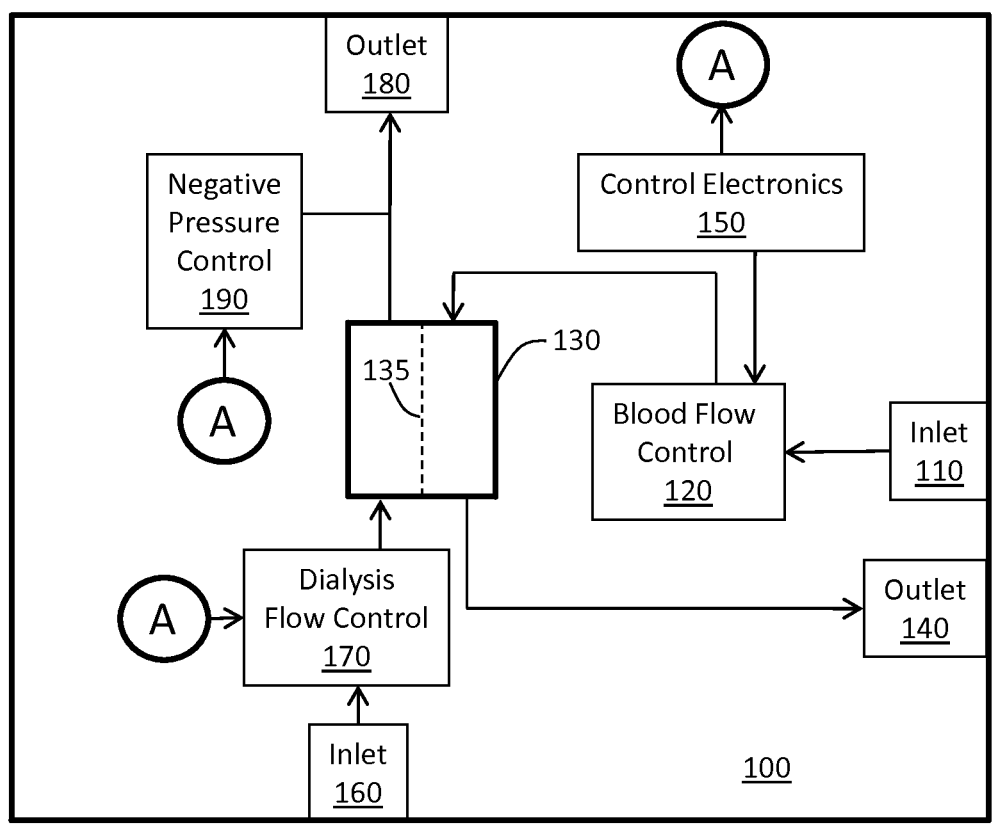
FIGS. 14-15 are schematic block diagrams of selected components of blood fluid removal devices or systems that may be employed in accordance with various embodiments presented herein.

Referring now to FIG. 14, a schematic block diagram of selected components of a blood fluid removal device 100 is shown. In the depicted embodiment, the device has in inlet 110 for receiving blood from a patient, a blood flow control element 120 in communication with the inlet 110 and configured to control the rate at which blood flows through medium 130 for removing fluid and contaminates from the blood. The device also includes an outlet 140 in communication with the medium 130 for returning blood to the patient. In the depicted embodiment, the medium 130 includes a semipermeable filter 135, such as a hemodialysis or hemodiafiltration filter. The membrane separates a blood flow compartment from a dialysis flow compartment of the medium 130. The device 100 has an inlet 160 for receiving fresh dialysate. Inlet 160 is in communication with a dialysis flow control element 170 for controlling the rate at which dialysis is introduced into the dialysis flow compartment of the medium 130. The device also has an outlet 180 in communication with the medium 130 for diverting used dialysate and fluid removed from the blood out of the device. In the depicted embodiment, the device also includes a negative pressure control element 190 in communication with the dialysate compartment of the medium component 130, as needed or desired. The device 100 also includes control electronics 150, which may include a processor, memory, etc., operably coupled to, and configured to control, the blood flow control element 120, the dialysis flow control element 170, and the negative pressure control element 190.

Based on information received from sensors that monitor blood fluid volume or tissue fluid volume, the control electronics 150 can control one or more of the blood flow control element 120 (e.g., based on calculated fluid volume removal prescription), the dialysis flow control element 170, and the negative pressure control element 190 to adjust the rate at which fluid is removed from the blood of the patient. For example, altering the flow rate of the blood (via the blood flow control element 120) through the medium component 130 may alter fluid clearance across the membrane. Altering flow of dialysate (via dialysis flow control element 170) through the medium component 130 may similarly alter fluid clearance across the membrane. Negative pressure (via negative pressure control element 190) may be applied on the dialysate compartment side of the membrane 135 and may result in greater fluid clearance across the membrane due to convective forces. It will be understood that a device 100 need not have all of the controllable elements (120, 170, 190) depicted in FIG. 15 to effectively control rate of fluid removal from blood based on data from sensors that monitor indicators of tissue fluid volume and blood fluid volume.

Any suitable blood flow control elements 120 may be used to control flow of blood through the membrane component 130. For example, a variable or adjustable rate pump may be employed. Alternatively or in addition, a series of electronically controllable valves in communication flow paths having differing resistance to flow may be employed (in such cases the flow restrictors would preferably be downstream of the medium component 130). Dialysis flow control element 170 may contain similar components or be similarly configured to blood flow control element 120. The negative pressure control element 120 may include a pump or the like.

Figure 15:
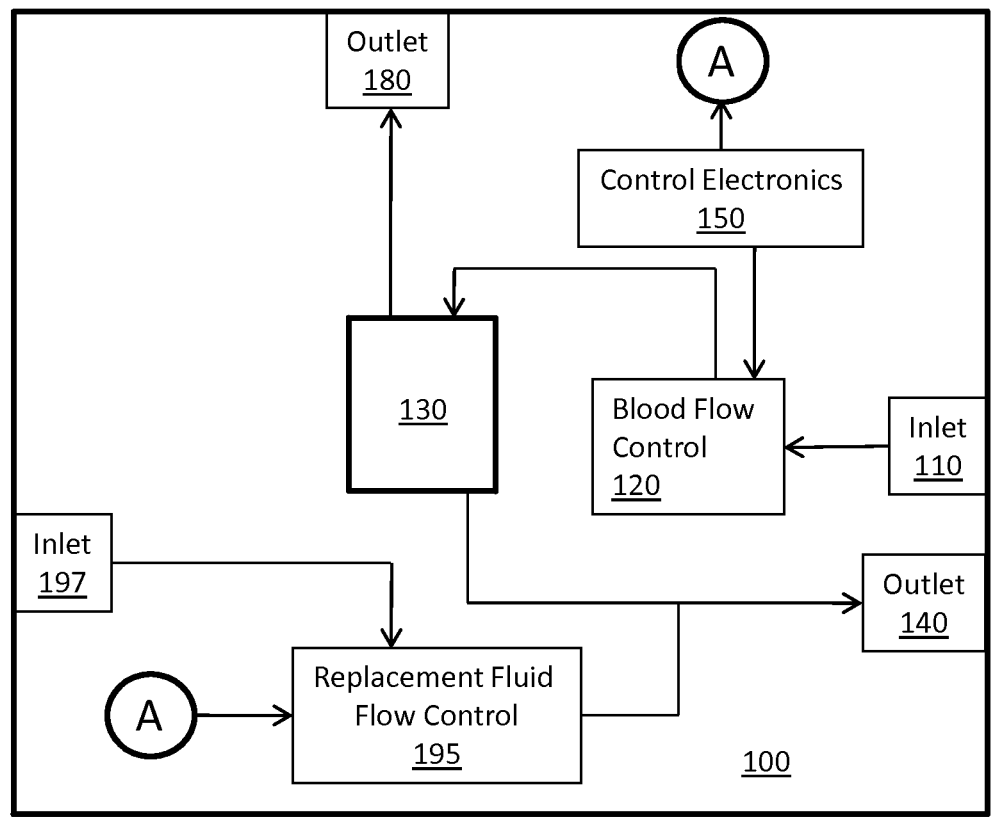

Referring now to FIG. 15, in which components that are numbered the same as in FIG. 17 refer to the same or similar components, the device 100 may include a fluid pathway for adding replacement fluid to blood before it is returned to the patient. The device 100 includes an inlet 197 for receiving the replacement fluid and a replacement fluid flow control element 195 in communication with the inlet and configured to control the rate at which the replacement fluid is added to the blood. The control electronics 150 are operable coupled to the replacement fluid flow control element 195 and are configured to control the rate at which replacement fluid flow control element 195 adds fluid to the blood based on data received from sensors that monitor blood fluid volume or tissue fluid volume. By controlling the rate at which fluid is introduced into blood, the rate of effective fluid removal from the blood is controlled.

Any suitable replacement fluid flow control element 195 may be used to control flow of replacement fluid into the blood before being returned to the patient. Replacement fluid flow control element 195 may contain similar components or be similarly configured to blood flow control element 120 as described above with regard to FIG. 15.

Figure 16:
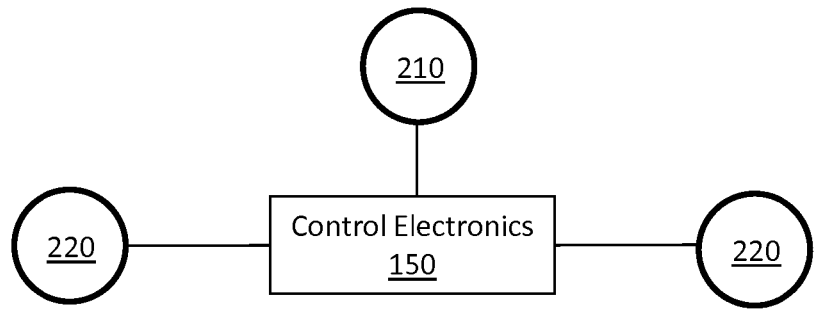
FIG. 16 is a schematic block diagram showing interactions between various sensors and control electronics.

As discussed above and as shown in FIG. 16, one or more sensing devices 200, 210, 220 or sensing components may communicate with control electronics 150 of a blood fluid removal device 100 or system. The communication may be direct or indirect. That is, a detector and appropriate electronics, such as filters, analog-to-digital converters or the like, may be directly coupled to sensing electronics 150 of the device 100 via a lead. Alternatively, a sensing device may acquire monitored data and transmit the data to the control electronics 150 of the device. In any case, the control electronics are configured to control the rate of fluid removal from blood based on the sensed information, e.g. as described above (e.g. based on calculated fluid volume removal prescription).

In some embodiments, a computer readable medium contains instructions that cause the processor of control electronics (of sensing device or fluid volume removal device) to carry out the methods described above, e.g. the methods depicted and described above with regard to FIGS. 7-9.

Of course, a sensing device may communicate with one or more intermediary device before data is sent to the blood fluid removal device or system to use the data to control the rate of fluid removal from blood in accordance with the teachings presented herein.

Various aspects of devices, systems, methods, computer-readable media, etc. are described herein. Some of the aspects are summarized below.

In a first aspect, a method comprises (i) monitoring an indicator of fluid volume of a patient via an implantable sensor device; and setting an initial fluid volume removal prescription for a blood fluid removal session based on the monitored indicator of fluid volume.

A second aspect is a method of the first aspect, further comprising transmitting data regarding the indicator of fluid volume from the implantable sensor device to fluid removal device.

A third aspect is a method of the second aspect, wherein setting the initial fluid volume removal prescription comprises calculating the fluid volume prescription by the fluid removal device based on the data received from the implantable sensor.

A fourth aspect is a method of any of aspects 1-3, wherein the indicator of fluid volume is an indicator of tissue fluid volume or an indicator of blood fluid volume.

A fifth aspect is a method of any of aspects 1-4, wherein the indicator of fluid volume is tissue impedance or blood hematocrit.

A sixth aspect is a method of any of aspects 1-5, wherein the indicator of fluid volume is tissue impedance.

A seventh aspect is a method of any of aspects 1-6, further comprising determining whether the indicator of fluid volume crosses a predetermined threshold value, and providing an alert to the patient if the indicator of fluid volume is determined to cross the threshold value.

An eighth aspect is a method of the seventh aspect, further comprising automatically scheduling a blood fluid removal session if the indicator crosses the threshold value by transmitting a signal from the sensor to a healthcare provider via an intermediary device.

A ninth aspect is a method of the first aspect, wherein monitoring the indicator of fluid volume comprises monitoring an indicator of tissue fluid volume, wherein the method further comprises monitoring an indicator of blood fluid volume, and wherein setting the initial fluid volume removal prescription for the blood fluid removal session based on the monitored indicator of fluid volume comprises setting the initial fluid volume removal prescription based on the ratio of the monitored indicators of tissue fluid volume and blood fluid volume.

A tenth aspect is a method of the first aspect, wherein monitoring the indicator of fluid volume comprises monitoring an indicator of blood fluid volume, wherein the method further comprises monitoring an indicator of tissue fluid volume, and wherein setting the initial fluid volume removal prescription for the blood fluid removal session comprises setting the initial fluid volume removal prescription based on the ratio of the monitored indicators of tissue fluid volume and blood fluid volume.

An eleventh aspect is a system comprising (a) a sensor configured to monitor an indicator of fluid volume; and (b) a blood fluid removal device comprising (i) an inlet for receiving blood from a patient, (ii) an first outlet for returning blood from the patient, (iii) a medium for removing fluid from the blood, the medium being positioned between the inlet and the first outlet, (iv) a fluid rate removal controller, (v) a second outlet for flow of the removed fluid, and (vi) electronics coupled to the fluid rate removal controller and the sensor, wherein the electronics are configured to set an initial fluid rate removal prescription based on data received from the sensor and to control the fluid rate removal controller based on the set initial fluid rate removal prescription.

A twelfth aspect is a system of the eleventh aspect, wherein the sensor is implantable.

A thirteenth aspect is a system of the eleventh aspect, wherein the sensor is wearable.

A fourteenth aspect is a system of any of aspects 11-13, wherein the electronics comprise a computer readable medium that, when implemented, cause the electronics to calculate the initial fluid rate removal prescription based on data received from the sensor and instruct the fluid rate removal controller to operate according to the initial fluid rate removal prescription.

A fifteenth aspect is a method of aspect 11 or 14, wherein the sensor and the fluid removal device are implantable.

A sixteenth aspect is a method of aspect 11 or 14, wherein the sensor and the fluid removal device are wearable.

A seventeenth aspect is a system of any of aspects 11-16, wherein the control electronics are disposed in a housing of the blood fluid removal device An eighteenth aspect is a method carried out by an implantable device comprising: (i) monitoring indicator of fluid volume in a patient suffering from chronic kidney disease, wherein the monitoring is performed, at least in part, by an implantable sensor device; (ii) determining whether the monitored indicator of fluid volume crosses a predetermined threshold; and (iii) providing a sensory cue to the patient if the monitored indicator is determined to cross the threshold.

A nineteenth aspect is a method of the eighteenth aspect, further comprising automatically scheduling a blood fluid removal session if the monitored indicator is determined to cross the threshold.

A twentieth aspect is a system comprising: (a) an implantable sensor device configured to monitor impedance of tissue of a patient, the device comprising (i) a first electrode, (ii) a second electrode, (iii) electronics operably coupled to the first and second electrodes for monitoring impedance of current flow between the two electrodes, and (iv) a first communication circuit configured to transmit data regarding the monitored impedance; (b) a fluid removal device for removing fluid from a patient, the device comprising (i) an inlet for receiving blood from a patient, (ii) a medium in for removing fluid from the blood, the medium being in communication with the inlet, (iii) an outlet in communication with the medium for returning blood to the patient; (iv) a flow controller in communication with the inlet, outlet or medium configured to control the rate at which the fluid is removed from the medium; (c) a second communication circuit configured to wirelessly receive the data regarding the impedance from the implantable device; and (d) electronics in communication with the second communication circuit and the flow controller wherein the electronics are configured to set an initial fluid removal prescription for a fluid removal session based on the impedance data received prior to the start of the session and to control the flow controller regarding the rate of fluid removal based on the received impedance data.

A twenty-first aspect is a system of the twentieth aspect, wherein the electronics of the fluid removal device are configured to alter the initial fluid removal rate or profile during a fluid removal session based on the on the impedance data received during the session.

A twenty-second aspect is a method of aspect 20 or 21, wherein the fluid removal device is implantable, and wherein the first communication circuit of the sensor device and the second communication circuit of the fluid removal device are the same circuit.

A twenty-third aspect is a system of any of aspects 20-22, wherein the control electronics are disposed in a housing of the blood fluid removal device.

A twenty-fourth aspect is a sensor device comprising: (i) a detector circuit and components configured to acquire sensed data regarding an indicator of fluid volume; (ii) control electronic configured to receive the acquired sensed data from the detector circuit and to calculate a fluid volume removal prescription based on the acquired sensed data.

EXAMPLE

The following prophetic example is presented to provide guidance as to how to acquire and interpret data from an implantable sensor configured to tissue fluid volume of a patient for use in methods or devices as described in the DETAILED DESCRIPTION above. It will be understood that the prophetic example provided herein in only one suitable way for monitored data to be acquired and interpreted in accordance with the general principles disclosed herein.

For this prophetic example, an implantable tissue impedance sensor, such as Medtronic, Inc.'s OptiVol® fluid status monitoring system, is implanted in a patient such that tissue impedance is measured between the housing of the device and an electrode extended from the housing via a lead. Well-documented procedures for determining acceptable ranges of tissue impedance and thus fluid volume have been established. See, e.g., (i) Siegenthalar, et al. Journal of Clinical Monitoring and Computing (2010): 24:449-451, and (ii) Wang, Am. J. Cardiology, 99(Suppl):3G-1-G, May 21, 2007. Such methods may be employed/Alternatively or in addition, tissue impedance may be monitored for a suitable period of time to establish as suitable baseline, and patient markers or clinician input may be used to instruct whether the patient is fluid overloaded or under-loaded. The data acquired by impedance sensor and input data regarding fluid status of the patient at the time the sensor data is acquired may be used to establish suitable ranges for impedance values. The sensor may be recalibrated from time to time by transmitting information regarding the fluid status of the patient determined, for example, as a result of a physical examination.

Once the sensor is properly calibrated, its readings with regard to tissue impedance as it relates to fluid volume may be trusted. These readings can then be reliably used in accordance with the teachings provided herein.

Thus, systems, devices and methods for MONITORING FLUID VOLUME FOR PATIENTS WITH RENAL DISEASE are described. Those skilled in the art will recognize that the preferred embodiments described herein may be altered or amended without departing from the true spirit and scope of the disclosure, as defined in the accompanying claims.

We claim:

1. A method comprising
monitoring an indicator of fluid volume of a patient via a sensor device wherein the indicator of fluid volume is interstitial fluid impedance;
monitoring an indicator of blood fluid volume;
setting an initial fluid volume removal prescription for a blood fluid removal session based on the monitored indicators of interstitial fluid volume and blood fluid volume.

2. The method of claim 1, further comprising transmitting data regarding the indicator of fluid volume and the indicator of blood fluid volume from the sensor device to a fluid removal device.

3. The method of claim 2, wherein setting the initial fluid volume removal prescription comprises calculating the fluid volume prescription by the fluid removal device based on the data received from the sensor.

4. The method of claim 2, wherein the fluid removal device is implantable.

5. The method of claim 2, wherein the fluid removal device is wearable.

6. The method of claim 1, further comprising determining whether the indicator of fluid volume crosses a predetermined threshold value, and providing an alert to the patient if the indicator of fluid volume is determined to cross the threshold value.

7. The method of claim 1, further comprising:
determining whether the monitored indicator of fluid volume crosses a predetermined threshold; and
providing a sensory cue to the patient if the monitored indicator is determined to cross the threshold.

8. The method of claim 1, wherein the sensor device comprises:
a detector circuit and components configured to acquire sensed data regarding an indicator of fluid volume; and
control electronics configured to receive the acquired sensed data from the detector circuit and to calculate a fluid volume removal prescription based on the acquired sensed data.

9. The method of claim 8, wherein the control electronics comprise a computer readable medium that, when implemented, cause the electronics to calculate the initial fluid rate removal prescription based on data received from the sensor and instruct the fluid rate removal controller to operate according to the initial fluid rate removal prescription.

10. A sensor device comprising:
a detector circuit and components configured to acquire sensed data regarding an indicator of fluid volume;
control electronics configured to receive the acquired sensed data from the detector circuit and to calculate a fluid volume removal prescription based on the acquired sensed data; wherein
the sensor device is configured to carry out the method of claim 8.

11. The method of claim 1, wherein setting an initial fluid volume removal prescription comprises a setting a volume rate of a replacement fluid that is added to a patient's blood.

12. The method of claim 1, further comprising setting an initial fluid rate removal prescription for the blood fluid removal session based on the monitored indicator of fluid volume.

13. The method of claim 12, setting the initial fluid rate removal prescription comprises calculating the fluid rate removal prescription by a fluid removal device based on the data received from the sensor.

14. The method of claim 1, wherein the sensor is configured to measure interstitial fluid impedance at a first location; and further comprising:
measuring interstitial fluid impedance at a second location; and
determining whether the impedance measured at the first location and the impedance measured at the second location differ by a predetermined amount.

15. The method of claim 1, wherein the sensor device is implantable.

16. The method of claim 1, wherein the sensor device is wearable.

17. The method of claim 1, wherein the initial fluid volume removal prescription is based on a ratio of the monitored indicators of interstitial fluid volume and blood fluid volume.

* * * * *